(12) United States Patent
De Sisternes et al.

(10) Patent No.: US 10,441,164 B1
(45) Date of Patent: Oct. 15, 2019

(54) CORRECTION OF DECORRELATION TAIL ARTIFACTS IN A WHOLE OCT-A VOLUME

(71) Applicant: Carl Zeiss Meditec, Inc., Dublin, CA (US)

(72) Inventors: Luis De Sisternes, San Francisco, CA (US); Homayoun Bagherinia, Oakland, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 37 days.

(21) Appl. No.: 15/914,933

(22) Filed: Mar. 7, 2018

Related U.S. Application Data

(60) Provisional application No. 62/469,245, filed on Mar. 9, 2017.

(51) Int. Cl.
*A61B 3/10* (2006.01)
*A61B 3/12* (2006.01)
*A61B 5/00* (2006.01)
*G06K 9/40* (2006.01)
*A61B 3/00* (2006.01)
(Continued)

(52) U.S. Cl.
CPC ............ *A61B 3/102* (2013.01); *A61B 3/1233* (2013.01); *A61B 3/1241* (2013.01); *A61B 5/0066* (2013.01); *A61B 5/7207* (2013.01); *A61B 5/7253* (2013.01); *A61B 3/0025* (2013.01); *A61B 5/02007* (2013.01); *G06K 9/40* (2013.01); *G06T 7/0012* (2013.01); *G06T 2207/10028* (2013.01); *G06T 2207/10101* (2013.01); *G06T 2207/20182* (2013.01); *G06T 2207/30041* (2013.01); *G06T 2207/30104* (2013.01)

(58) Field of Classification Search
CPC .......... A61B 3/14; A61B 3/0025; A61B 3/12; A61B 3/102; A61B 3/0008
USPC ........................................................ 351/206
See application file for complete search history.

(56) References Cited

U.S. PATENT DOCUMENTS 7,301,644 B2  11/2007  Knighton et al.
8,332,016 B2  12/2012  Stetson
(Continued)

FOREIGN PATENT DOCUMENTS

WO      2017/027844 A1      2/2017

OTHER PUBLICATIONS

An et al., "In Vivo Volumetric Imaging of Vascular Perfusion within Human Retina and Choroids with Optical Micro-Angiography", Optics Express, vol. 16, No. 15, Jul. 21, 2008, pp. 11438-11452.
(Continued)

*Primary Examiner* — Mohammed A Hasan
(74) *Attorney, Agent, or Firm* — Morrison & Foerster LLP

(57) ABSTRACT

A method and system for correction of decorrelation tail artifacts in optical coherence tomography (OCT) angiography volumetric data defines a movable target subvolume within the OCT-A volumetric data. The target subvolume is axially moveable within the OCT-A volumetric data in discrete axial steps. At each axial step, a reference subvolume corresponding to a depth location in the OCT A volumetric data is defined axially offset from the target subvolume. The reference subvolume may be defined within the OCT A volumetric data, or defined within a different (previously corrected) OCT-A volume. Irrespective, corrected OCT-A data that corrects for decorrelation tail arti-
(Continued)

facts in the target subvolume is defined using information in the reference subvolume and information in the target subvolume.

20 Claims, 11 Drawing Sheets

(51) Int. Cl.
  *G06T 7/00* (2017.01)
  *A61B 5/02* (2006.01)

(56) References Cited

U.S. PATENT DOCUMENTS

| | | | |
|---|---|---|---|
| 9,332,902 | B2 | 5/2016 | Tumlinson et al. |
| 2008/0025570 | A1 | 1/2008 | Fingler et al. |
| 2010/0027857 | A1 | 2/2010 | Wang |
| 2012/0307014 | A1 | 12/2012 | Wang |
| 2017/0169590 | A1 | 6/2017 | Huang et al. |
| 2017/0319060 | A1 | 11/2017 | Huang et al. |

OTHER PUBLICATIONS

Blazkiewicz et al., "Signal-To-Noise Ratio Study of Full-Field Fourier-Domain Optical Coherence Tomography", Applied Optics, vol. 44, No. 36, Dec. 20, 2005, pp. 7722-7729.

Enfield et al., "In Vivo Imaging of the Microcirculation of the Volar Forearm using Correlation Mapping Optical Coherence Tomography (cmOCT)", Biomedical Optics Express, vol. 2, No. 5, 2011, pp. 1184-1193.

Fingler et al., "Mobility and Transverse Flow Visualization using Phase Variance Contrast with Spectral Domain Optical Coherence Tomography", Optics Express, vol. 15, No. 20, 2007, pp. 12636-12653.

Hillmann et al., "Holoscopy-Holographic Optical Coherence Tomography", Optics Letters, vol. 36, No. 13, Jul. 1, 2011, pp. 2390-2392.

Jia et al., "Quantitative Optical Coherence Tomography Angiography of Choroidal Neovascularization in Age-Related Macular Degeneration", American Academy of Ophthalmology, vol. 121, No. 7, Jul. 2014, pp. 1435-1444.

Jia et al., "Split-Spectrum Amplitude-Decorrelation Angiography with Optical Coherence Tomography", Optics Express, vol. 20, No. 4, 2012, pp. 4710-4725.

Mariampillai et al., "Speckle Variance Detection of Microvasculature using Swept-Source Optical Coherence Tomography", Optics Letters, vol. 33, No. 13, Jul. 1, 2008, pp. 1530-1532.

Nakamura et al., "High-Speed Three-Dimensional Human Retinal Imaging by Line-Field Spectral Domain Optical Coherence Tomography", Optics Express, vol. 15, No. 12, 2007, pp. 7103-7116.

Spaide et al., "Image Artifacts in Optical Coherence Tomography Angiography", Retina, vol. 35, No. 11, 2015, pp. 2163-2180.

Zhang et al., "Minimizing Projection Artifacts for Accurate Presentation of Choroidal Neovascularization in OCT Micro-Angiography", Biomedical Optics Express, vol. 6, No. 10, 2015, pp. 4130-4143.

Zhang et al., "Projection-Resolved Optical Coherence Tomographic Angiography", Biomedical Optics Express, vol. 7, No. 3, 2016, pp. 816-828.

CORRECTION OF DECORRELATION TAIL ARTIFACTS IN A WHOLE OCT-A VOLUME

PRIORITY

This application claims priority to U.S. Provisional Application Ser. No. 62/469,245 filed Mar. 9, 2017, the contents of which are hereby incorporated by reference.

BACKGROUND

Optical coherence tomography (OCT) is a noninvasive, noncontact imaging modality that uses coherence gating to obtain high-resolution cross-sectional images of tissue microstructure. Several implementations of OCT have been developed. In frequency domain OCT (FD-OCT), the interferometric signal between light from a reference and the back-scattered light from a sample point is recorded in the frequency domain typically either by using a dispersive spectrometer in the detection arm in the case of spectral-domain OCT (SD-OCT) or rapidly tuning a swept laser source in the case of swept-source OCT (SS-OCT). After a wavelength calibration, a one-dimensional Fourier transform is taken to obtain the scattering profile of a sample along the OCT beam. Each scattering profile is called an axial scan, or A-scan. Cross-sectional images, called B-scans, and by extension 3D volumes, are built up from many A-scans, with the OCT beam illuminating a set of transverse locations on the sample either by scanning or field illumination.

Functional OCT can provide important clinical information that is not available in the typical intensity based structural OCT images. There have been several functional contrast enhancement methods including Doppler OCT, Phase-sensitive OCT, Polarization Sensitive OCT, Spectroscopic OCT, etc. Integration of functional extensions can greatly enhance the capabilities of OCT for a range of applications in medicine.

One of the most promising functional extensions of OCT has been the field of OCT angiography which is based on flow or motion contrast between repeated structural OCT measurements. A variety of OCT Angiography techniques have been developed including but not limited to optical microangiography (OMAG), speckle variance, phase variance, correlation mapping, and decorrelation (see for example US Patent Publication No. 2008/0025570, US Patent Publication No. 2010/0027857, US Patent Publication No. 2012/0307014, Fingler et al. "Mobility and transverse flow visualization using phase variance contrast with spectral domain optical coherence tomography" Opt. Express 2007; 15:12636-53, Mariampillai et al., "Speckle variance detection of microvasculature using swept-source optical coherence tomography", Optics Letters 33(13), 1530-1533, 2008, An et al., "In vivo volumetric imaging of vascular perfusion within human retina and choroids with optical micro-angiography," Opt. Express 16(15), 11438-11452, 2008, Enfield et al., "In vivo imaging of the microcirculation of the volar forearm using correlation mapping optical coherence tomography" (cmOCT), Biomed. Opt. Express 2(5), 1184-1193, 2011, and Jia et al. "Split-spectrum amplitude decorrelation angiography with optical coherence tomography" Optics Express 20(4) 4710-4725 (2012), the contents of all of which are hereby incorporated by reference). These techniques use the OCT data to achieve the imaging of functional vascular networks within microcirculatory tissue beds in vivo, without the use of exogenous contrast agents.

The key point of OCT angiography processing methods is to extract localized signal variations from the bulk motion signal of a background tissue by comparing OCT signals, such as B-scans, captured at different closely-spaced time points (inter-frame change analysis). Processing can be carried out on the complex OCT data (complex-based), the amplitude or intensity portion of the OCT data (intensity-based), or the phase portion of the data (phase-based). The separately processed intensity and phase information can also be combined in some approaches. One of the major applications of flow contrast techniques (e.g., intensity-based, phase-based, complex-based, etc.) has been to generate en face vasculature images of the retina (angiograms). High resolution en face visualization based on inter-frame change analysis requires high density of sampling points and hence the time required to finish such scans can be up to an order of magnitude higher compared to regular cube scans used in commercial OCT systems.

One of the major limitations of OCT angiography is the occurrence of projection artifacts, or decorrelation tail artifacts, in the OCT angiography images. Light passing through a blood vessel can be reflected, refracted, or absorbed. The light reflected from blood moving in the vessels forms the basis of optical coherence tomography angiography (OCT-A). However, the light that has passed through moving blood also encounters tissue below the blood vessel. When this light strikes the deeper layers in the eye, such as the retinal pigment epithelium (RPE) layer, it is reflected back to the OCT instrument. The light that has passed through the blood vessels changes over time, and so the reflected portion of this light is detected as having a decorrelation resembling blood flow. Therefore, the RPE will seem to have blood vessels that have the pattern of the overlying retinal blood vessels. This effect is referred to as the OCT-A projection artifact. OCT-A projection artifacts also occur from superficial retinal vessels, which can be seen in deeper retinal layers, or retinal and choroidal vessels which can be even seen deep in the sclera. OCT-A projection artifacts are nearly always present and seen in any structure that is located below vasculature.

One of the steps in a standard OCT angiography algorithm involves producing 2D angiography vasculature images (angiograms) of different regions or slabs of the tissue along the depth dimension from the obtained flow contrast images, which may help a user to visualize vasculature information from different retinal layers. A slab image can be generated by summing, integrating, taking the minimum or maximum value or other techniques to determine or select a single representative value of the cube motion contrast data along a particular axis between two layers (see for example U.S. Pat. Nos. 7,301,644 and 8,332,016, the contents of both of which are hereby incorporated by reference). The slabs that are most affected by decorrelation tail artifacts may include, for example, Deeper Retinal Layer (DRL), Avascular Retinal Layer (ARL), Choriocapillaris Layer (CC), and any custom slabs, especially the ones that contain the RPE.

FIG. 1 shows exemplary slab images of a superficial retinal layer (SRL) 106 and a deeper retinal layer (DRL) 108 generated as a result of segmenting OCT angiographic data, having a representative B-scan 102. The segmented B-scan 102 shows the inner limiting membrane (ILM), as indicated by reference numeral 103, the inner plexiform layer (IPL), as indicated by reference numeral 104, and the outer plexiform layer (OPL), as indicated by reference numeral 105. The upper slab image (SRL) 106 is the result of the summation of the motion contrast data between the ILM 103 and the IPL 104. The lower slab image (DRL) 108 is the result of the summation of the motion contrast data between the IPL 104 and the OPL 105. As depicted, the decorrelation tail effect, as indicated for example by reference numerals 110a-c, is visible in the image of the DRL 108. The large vessels in the SRL image 106 appear in DRL image 108 as weaker vessel artifacts.

Some of the previous methods that are used to reduce the projection artifacts include:

1) Subtracting an angiogram generated based on deeper layers from the angiogram generated from the superficial layers directly after some preprocessing steps. In this method, a true angiographic image for the subretinal space can be obtained by a simple subtraction of a scaled image obtained from the retinal space from the image obtained from the subretinal space (see for example, Zhang, Anqi, Qinqin Zhang, and Ruikang K. Wang. "Minimizing projection artifacts for accurate presentation of choroidal neovascularization in OCT micro-angiography." *Biomedical Optics Express* 6.10 (2015): 4130-4143.).

2) Removing flow projection artifacts from superficial retinal blood vessels to the outer retina by first generating a binary large inner retinal vessel map based on applying a 30×30 pixel Gaussian filter. This filter removed small inner retinal vessels and masked the outer retina flow map, thus enabling the subtraction of large vessel projections. A binary outer retinal flow map was then generated by applying a 10×10 pixel Gaussian filter to remove remaining noise and mask the outer retinal flow map again to obtain a clear map. After these artifacts are removed by the mask subtraction operation, there were no longer any flow artifacts in the normally avascular outer retina (see for example, Jia, Yali, et al. "Quantitative optical coherence tomography angiography of choroidal neovascularization in age-related macular degeneration." *Ophthalmology* 121.7 (2014): 1435-1444, Zhang, M., Hwang, T. S., Campbell, J. P., Bailey, S. T., Wilson., D. J Huang, D., & Jia, Y. (2016). Projection-resolved optical coherence tomographic angiography. *Biomedical optics express,* 7(3), 816-828).

3) Slab-based approach (e.g., traditional slab-based correction method/approach), in which an artifact-present slab (topographic projection of the OCT-A volume within two defined surfaces) to be displayed without artifacts is corrected using the information of an additional slab (reference slab) defined in an upper depth position (i.e., inner locations with respect to the retina). It is assumed that the deeper slab image is generated by mixing the upper reference slab and the artifact-free slab (the unknown image to reconstruct). Artifacts can then be removed using a particular mixing model that could be of additive or multiplicative nature. Even though this traditional slab-based correction method for artifact correction works pretty well, there are still some limitations that call for a further improved approach for artifact correction. Some of the limitations associated with the traditional slab-based correction solution include 1) both the slab to be corrected and the reference slab are governed by the definition of two surfaces, which are typically defined by an automated segmentation algorithm. Possible errors in the segmentation and/or unknowns in the relationship of both slabs may lead to the removal of important information in the corrected slab (for example, actual blood vessels that are partially present in both the correction and reference slab) or the non-removal of severe artifacts (for example, those artifacts due to vessels that are not present in the reference slab due to its definition), 2) the traditional slab-based correction approach works satisfactorily for slabs generated using a maximum projection method when the surfaces describing the target and reference slabs are defined a priori based on structural information. However, this may not be the case when using, for example, a summation projection method to generate the slabs. As the decorrelation tail artifacts propagate deeper into the volume, they may overpower the real signal when using a thick slab definition. This causes the masking of the real signal in the slab and the inability to display it even after the artifacts are corrected, 3) it does not allow the development of three-dimensional techniques for the automated determination of optimal slabs for pathology visualization, and neither allows segmentation, quantification and visualization of vascular pathologies within the OCT-A volume, 4) it assumes a sub-optimal processing workflow where an artifact-correction algorithm must be executed every time there is a change in the slab definition, no matter how minimal this change is or if the definition is reverted to a previous step. This translates to increased processing time and memory as a user displaces the surfaces defining a slab to visualize particular vessels of interest.

Therefore, what is needed is an improved artifact reduction/correction method that can overcome the above discussed problems of the previous methods and allow the generation of artifact-free OCT-A topographic images by different projection methods, as well as allowing automated slab optimization, segmentation, quantification and visualization of pathologies within an OCT-A volume.

SUMMARY

In embodiments, a method and system is provided for correction of decorrelation tail artifacts (e.g., projection artifacts) in optical coherence tomography (OCT) angiography (OCT-A) volumetric data. In embodiments, OCT-A volumetric data may be obtained by collecting three dimensional OCT data of an eye from an OCT system, and calculating motion contrast information in the three dimensional OCT data using an OCT-A processing technique. Decorrelation tail artifact may refer to a projection artifact due to a blood vessel (e.g., blood movement) in an upper retinal layer projecting itself onto a lower retinal layer, such as by casting a shadow on, or otherwise interfering with, the OCT or OCT-A volumetric data of the lower layer. As it is known in the art, OCT or OCT-A data is a collection of individual A-scans that collectively define a volume, and each A-scan is identified by an x-y coordinate on a plane perpendicular to an axial axis (z-coordinate) directed toward (or into) an eye. That is, the x-y coordinate plane (or horizontal-vertical plane) commonly describes an en face plane. Therefore, the term OCT-A volumetric data is herein applicable to an A-scan, B-scan and/or 3D volume (e.g., cube). That is, the present method may be applied to an A-scan, B-scan, or 3D volume of OCT-A volumetric data, but for ease of discussion, the term "volume" is freely used to apply to any of an A-scan, B-scan, or 3D volume, unless otherwise specified or understood from context. Thus, the present method removes decorrelation tail artifacts independent of any slab definition or segmentation for both healthy and disease subjects.

Volume correction may be done by axially (e.g., in the z-direction) moving a sliding window (that defines a target subvolume within the OCT-A volumetric data), such as from top (e.g., an upper retinal layer) towards the bottom (e.g., a lower layer retinal layer) of the OCT-A volumetric data (or "volume" for ease of discussion) in sequential steps. It is to be understood that the window may be a length window (e.g., a contiguous linear segment) of data (e.g., pixels) in the case of an A-scan, or may be an area window in the case of a B-scan, or a volume window or a traversing plane window (e.g., an en face plane) in the case of a 3D volume. Volume locations covered/defined by such a window (e.g., target subvolume) may be corrected using current OCT-A information from the current window and OCT-A information from a second window (e.g., a reference subvolume) axially offset from the current window (e.g., target subvolume). The OCT-A information from the second window may be taken from the current OCT-A volumetric data, or from a different (e.g., a previously corrected) OCT-A data volume. For example, in embodiments, a record of corrected windows may be maintained separately (and optionally appended together) to define a corrected OCT-A data volume (or image) that grows as each newly corrected window is collected (e.g., appended). In embodiments, volume locations defined by a current window in the current OCT-A volumetric data may be corrected using OCT-A information from the current window and from previously corrected OCT-A information corresponding to the second window (reference subvolume), which defines the axially offset position in the corrected OCT-A data volume. Thus, the axially offset OCT-A information used to correct the current OCT-A information may have been corrected in a previous step, or iteration.

In embodiments, the corrections may be appended to the corrected OCT-A data volume. Alternatively, the original OCT-A volumetric data may be updated based on the corrected OCT-A data. For example, a region of the OCT-A volumetric data corresponding to the first window (i.e. the target subvolume) may be corrected based on (e.g. overwritten with) the corrected data. That is, corrections may be done in a projected axial summation of a subvolume covered by the sliding window, and set back to cover (e.g., overwrite) the original target subvolume with the corrected subvolume, once corrected.

In embodiments, decorrelation tail artifacts in OCT-A volumetric data of an eye may be corrected in a method or system that defines a target subvolume within the OCT-A volumetric data. The target subvolume may have an axial depth and be axially moveable within the OCT-A volumetric data. That is, the target subvolume may correspond to the sliding window mentioned above. The target subvolume may be moved in discrete axial steps within the OCT-A volumetric data, and at each axial step: (a) a reference subvolume corresponding to a depth location in the OCT-A volumetric data may be defined axially offset from the target subvolume; and (b) corrected OCT-A data that corrects for decorrelation tail artifacts in the target subvolume may be defined using information in the reference subvolume and information in the target subvolume. The corrected OCT-A volumetric data may then be displayed or stored or submitted to further analysis.

As mentioned above, the reference subvolume may correspond to the OCT-A volumetric data being corrected, or may correspond to a growing, corrected OCT-A data volume. That is, in some embodiments, at each axial step mentioned immediately above: (c) a positional correspondence between the defined corrected OCT-A data and the OCT-A volumetric data within the target subvolume may be determined; and (d) the OCT-A volumetric data within the target subvolume may be updated (e.g., overwritten) based on its corresponding corrected OCT-A data. In this case, the reference subvolume may be defined within the OCT-A volumetric data, itself. In some embodiments, an empty volume to serve as a corrected OCT-A volume may first be initialized. Then, at each axial step; (c) the corrected OCT-A volume with the defined corrected OCT-A data may be updated at an updated depth location within the corrected OCT-A volume. The updated depth location with the corrected OCT-A volume may then be mapped to the current depth location of the target subvolume within the OCT-A volumetric data. In this case, the reference subvolume may be defined within the corrected OCT-A volume, and optionally not within the original OCT-A volumetric data.

In embodiments, the reference subvolume may be moved axially in discrete steps, and the size of each discrete step may be fixed or variable. Different size steps may affect the speed with which the present method is applied.

In embodiments, the reference subvolume may define an area/volume that at least partially overlaps that of the target subvolume, or may completely avoid the target subvolume. In embodiments, the target subvolume may be made to move from top to bottom of the original OCT-A volumetric data, or may be made to span only a target axial range within the OCT-A volumetric data, if only a portion of the OCT-A volumetric data is to be corrected.

The depth span of the target subvolume and/or reference subvolume may be fixed or variable. For example, the depth span of the target subvolume and the reference subvolume may be equal to each other, or different from each other, at each axial step. Additionally, the depth span of either of the target subvolume or reference subvolume may be independently changed from (axial) step-to-step.

According to another aspect of the subject matter described in the present application, a method for correcting decorrelation tail artifacts in optical coherence tomography (OCT) angiography volumetric data of an eye includes (1) collecting three dimensional OCT image data of the eye from an OCT system; (2) calculating motion contrast information in the three dimensional OCT image data using an OCT angiography (OCT-A) processing technique to obtain an OCT-A volume cube, said OCT-A volume cube containing the decorrelation tail artifacts; (3) defining a target subvolume to correct from the OCT-A volume cube at a particular depth location (k·S) with a predetermined axial width (W), where k is an iterative value that starts with value 0 and increases serially (k=k+1) with each iteration and S is a parameter defining step size; (4) defining a reference subvolume from the corrected volume at a depth location (k·S−T), where T is a correction margin that enables a small margin of separation between the target volume and reference volume; (5) projecting the target subvolume and the reference subvolume to corresponding target and reference maps using a projection technique; (6) correcting the decorrelation tail artifacts in the target map using information in the reference map and updating the target subvolume in the OCT-A volume based on the corrected target map; (7) repeating steps (3)-(6) until the entire OCT-A volume is corrected; and (8) displaying or storing the corrected OCT-A volume or a further analysis thereof.

The artifact correction method described in the present application is particularly advantageous in a number of respects. By way of example and not limitation, (1) it corrects a whole OCT-A volume instead of a previously defined slab and is independent of any slab definition or segmentation, and therefore unaffected by possible segmentation errors, (2) it uses information that has already been corrected as reference and also implicitly considers the width of the vessel in such reference information, (3) allows generation of optimal slabs from the corrected volume for the visualization of particular pathologies, automatically or semi-automatically adapted to each particular case, and (4) a better workflow in general, where the whole cube is corrected first and artifact-free slabs can be generated directly from it without the need of executing any correction algorithm for any desired slab.

Further aspects include various additional features and operations associated with the above and following aspects and may further include, but are not limited to corresponding systems, methods, apparatus, and computer program products.

The features and advantages described herein are not all-inclusive and many additional features and advantages will be apparent to one of ordinary skill in the art in view of the figures and description. Moreover, it should be noted that the language used in the specification has been principally selected for readability and instructional purposes and not to limit the scope of the inventive subject matter.

BRIEF DESCRIPTION OF THE DRAWINGS

FIG. 7A shows the originally produced slab with artifacts. FIG. 7B shows the slab after the traditional slab-based correction method and FIG. 7C shows the slab after applying the OCT-A volume correction method of the present disclosure.

FIG. 8A shows the originally produced slab with artifacts. FIG. 8B shows the slab after the traditional slab-based correction method and FIG. 8C shows the slab after applying the OCT-A volume correction method of the present disclosure.

FIG. 9A shows the originally produced slab with artifacts. FIG. 9B shows the slab after the traditional slab-based correction method and FIG. 9C shows the slab after applying the OCT-A volume correction method of the present disclosure.

DETAILED DESCRIPTION

All patent and non-patent references cited within this specification are herein incorporated by reference in their entirety to the same extent as if the disclosure of each individual patent and non-patent reference was specifically and individually indicated to be incorporated by reference in its entirety.

Example OCT System

Figure 1:
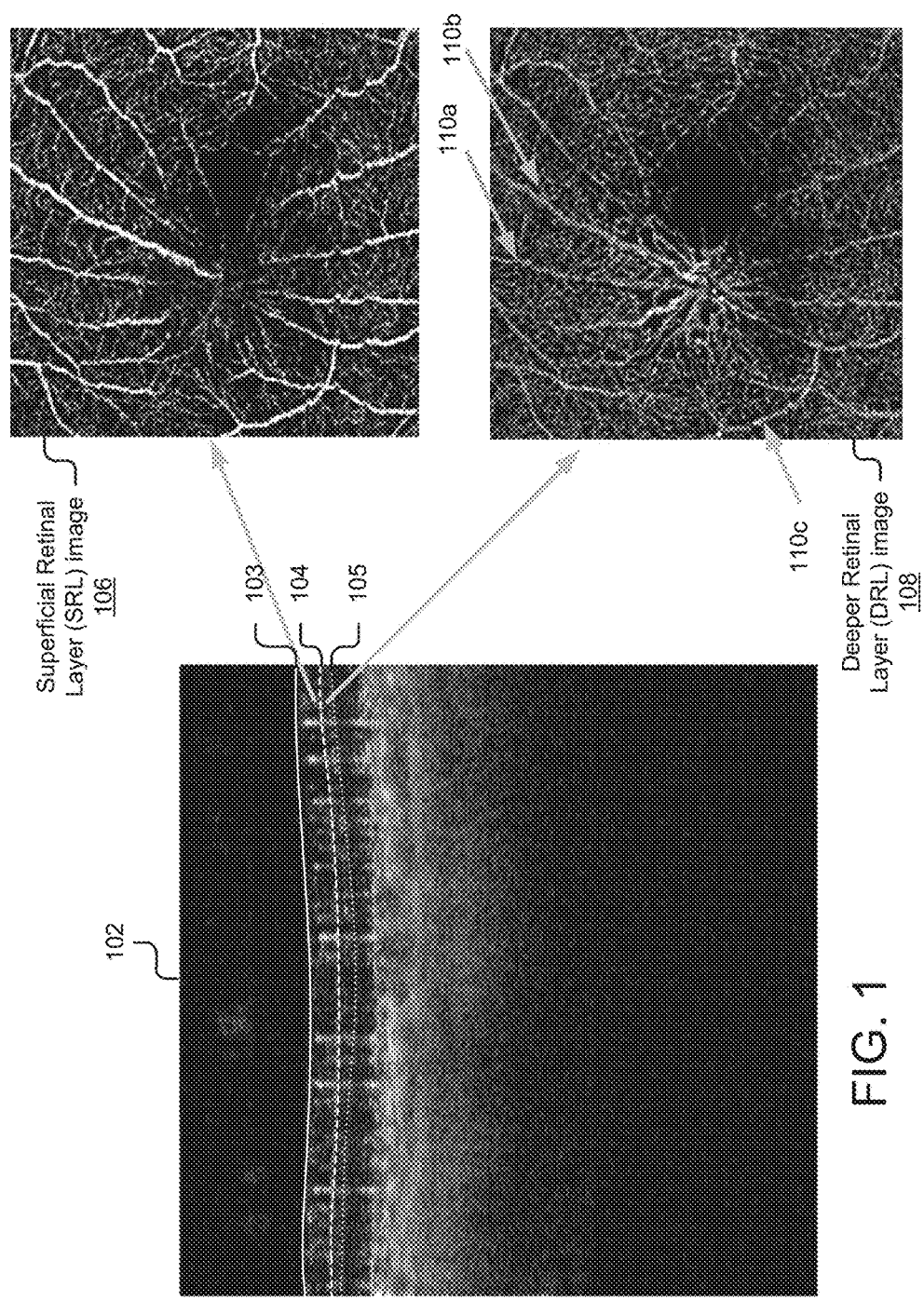
FIG. 1 is an example illustration showing segmentation of an OCT angiographic data (B-scan) to produce a superficial retinal layer image and a deeper retinal layer image. The deeper retinal layer image contains decorrelation tail artifacts.
Figure 2:
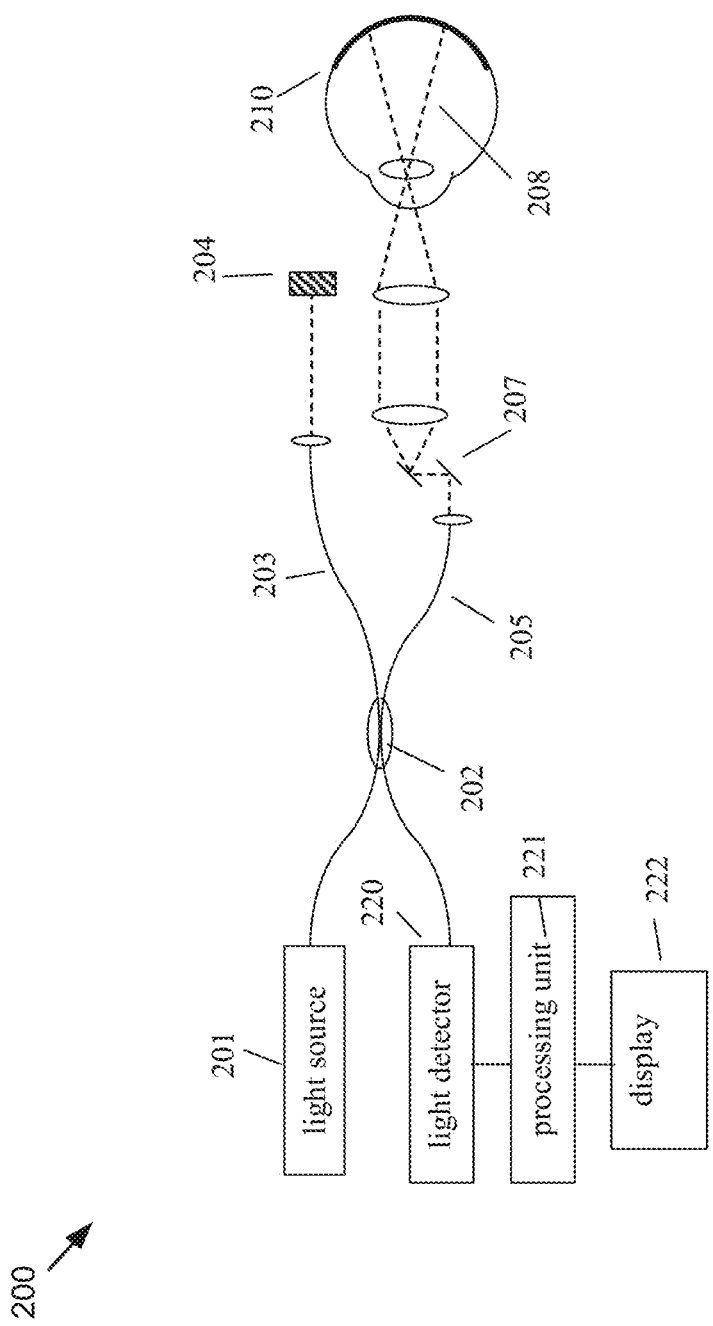
FIG. 2 is a generalized optical coherence tomography (OCT) system suitable for use with the present invention.

A generalized FD-OCT system used to collect 3-D image data of the eye suitable for use with the present invention is illustrated in FIG. 2. An FD-OCT system 200 includes a light source, 201, typical sources including but not limited to broadband light sources with short temporal coherence lengths or swept laser sources. A beam of light from source 201 is routed, typically by optical fiber 205, to illuminate the sample 210, a typical sample being tissues in the human eye. The source 201 can be either a broadband light source with short temporal coherence length in the case of SD-OCT or a wavelength tunable laser source in the case of SS-OCT. The light is scanned, typically with a scanner 207 between the output of the fiber and the sample, so that the beam of light (dashed line 208) is scanned laterally (in x and y) over the region of the sample to be imaged. Light scattered from the sample is collected, typically into the same fiber 205 used to route the light for illumination. Reference light derived from the same source 201 travels a separate path, in this case involving fiber 203 and retro-reflector 204 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 202, to form light interference in a detector 220. Although a single fiber port is shown going to the detector, those skilled in the art recognize that various designs of interferometers can be used for balanced or unbalanced detection of the interference signal. The output from the detector 220 is supplied to a processor 221 that converts the observed interference into depth information of the sample. The results can be stored in the processor 221 or other storage medium or displayed on display 222. The processing and storing functions may be localized within the OCT instrument or functions may be performed on an external processing unit (e.g., the computer system 1000 shown in FIG. 11) to which the collected data is transferred. This unit could be dedicated to data processing or perform other tasks which are quite general and not dedicated to the OCT device. The processor 221 may contain for example a field-programmable gate array (FPGA), a digital signal processor (DSP), an application specific integrated circuit (ASIC), a graphics processing unit (GPU), a system on chip (SoC) or a combination thereof, that performs some, or the entire data processing steps, prior to passing on to the host processor or in a parallelized fashion.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. Instead of mechanically scanning the beam, a field of light can illuminate a one or two-dimensional area of the retina to generate the OCT data (see for example, U.S. Pat. No. 9,332,902; D. Hillmann et al, "Holoscopy—holographic optical coherence tomography" *Optics Letters* 36(13): 2390 2011; Y. Nakamura, et al, "High-Speed three dimensional human retinal imaging by line field spectral domain optical coherence tomography" *Optics Express* 15(12):7103 2007; Blazkiewicz et al, "Signal-to-noise ratio study of full-field Fourier-domain optical coherence tomography" *Applied Optics* 44(36):7722 (2005)). In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system. Various aspects of the invention could apply to other types of ophthalmic diagnostic systems and/or multiple ophthalmic diagnostic systems including but not limited to fundus imaging systems, visual field test devices, and scanning laser polarimeters.

In Fourier Domain optical coherence tomography (FD-OCT), each measurement is the real-valued spectral interferogram ($S_j(k)$). The real-valued spectral data typically goes through several postprocessing steps including background subtraction, dispersion correction, etc. The Fourier transform of the processed interferogram, results in a complex valued OCT signal output $A_j(z)=|A_j|e^{i\varphi}$. The absolute value of this complex OCT signal, $|A_j|$, reveals the profile of scattering intensities at different path lengths, and therefore scattering as a function of depth (z-direction) in the sample. Similarly, the phase, $\varphi_j$ can also be extracted from the complex valued OCT signal. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. We use the term "cluster scan" herein to refer to a single unit or block of data generated by repeated acquisitions at the same location for the purposes of analyzing motion contrast. A cluster scan can consist of multiple A-scans or B-scans collected with relatively short time separations at approximately the same location(s) on the sample. A variety of ways to create B-scans are known to those skilled in the art including but not limited to along the horizontal or x-direction, along the vertical or y-direction, along the diagonal of x and y, or in a circular or spiral pattern. The majority of the examples discussed herein refer to B-scans in the x-z dimensions but the invention would apply equally to any cross sectional image.

The OCT system may use any one of a number of OCT Angiography processing algorithms on one or more cluster scans of OCT data collected at the same or approximately the same transverse locations on a sample at different times. As previously mentioned, motion contrast algorithms can be applied to the intensity information derived from the image data (intensity-based algorithm), the phase information from the image data (phase-based algorithm), or the complex image data (complex-based algorithm). An en face vasculature image is an image displaying motion contrast signal in which the data dimension corresponding to depth is displayed as a single representative value, typically by summing or integrating all or an isolated portion of the data.

The OCT system discussed herein may provide 2D (i.e. cross-sectional) images, en-face images, 3-D images, metrics related to a health condition, and the like. This system may be used with any other system. For example, the OCT system may be used with a surgical system or surgical microscope system for diagnostic or treatment purposes. The OCT system may be used to analyze any sample. For example, the OCT system may be used in analysis, e.g. formation of images, of, for example, any type of life forms and inanimate objects. Examples of life forms may be animals, plants, cells or the like.

Decorrelation Tail Artifact Correction in Whole OCT-A Volume

As discussed elsewhere herein, optical coherence tomography angiography (OCT-A) is prone to decorrelation tail artifacts due to the high scattering property of blood within overlying patent vessels, creating artifacts that interfere with the interpretation of retinal angiographic results. In other words, deeper layers may have projection artifacts due to fluctuating shadows cast by flowing blood in large inner retinal vessels above them that may cause variation in the reflected signal. This signal variation is detected as a decorrelation and may be difficult to differentiate from true flow.

In embodiments, a method that is independent of segmentation lines and slab definitions is provided for the correction of decorrelation tail artifacts in OCT-A data (e.g., A-scan, B-scan, and/or volume). The method may include a set of serial consecutive steps in which a corrected portion or full volume gets updated. At each step, a thin (small axial span/thickness) portion of the OCT-A volume (subvolume) may be partially corrected using a portion of the volume that has already been corrected in a previous step as reference. The subvolume considered at each step may be located at increasing depths in an overlapping manner. Each pixel within the volume may then be corrected in several consecutive steps defined by this overlap. This approach is further discussed in detail below with respect to FIG. 3.

Figure 3:
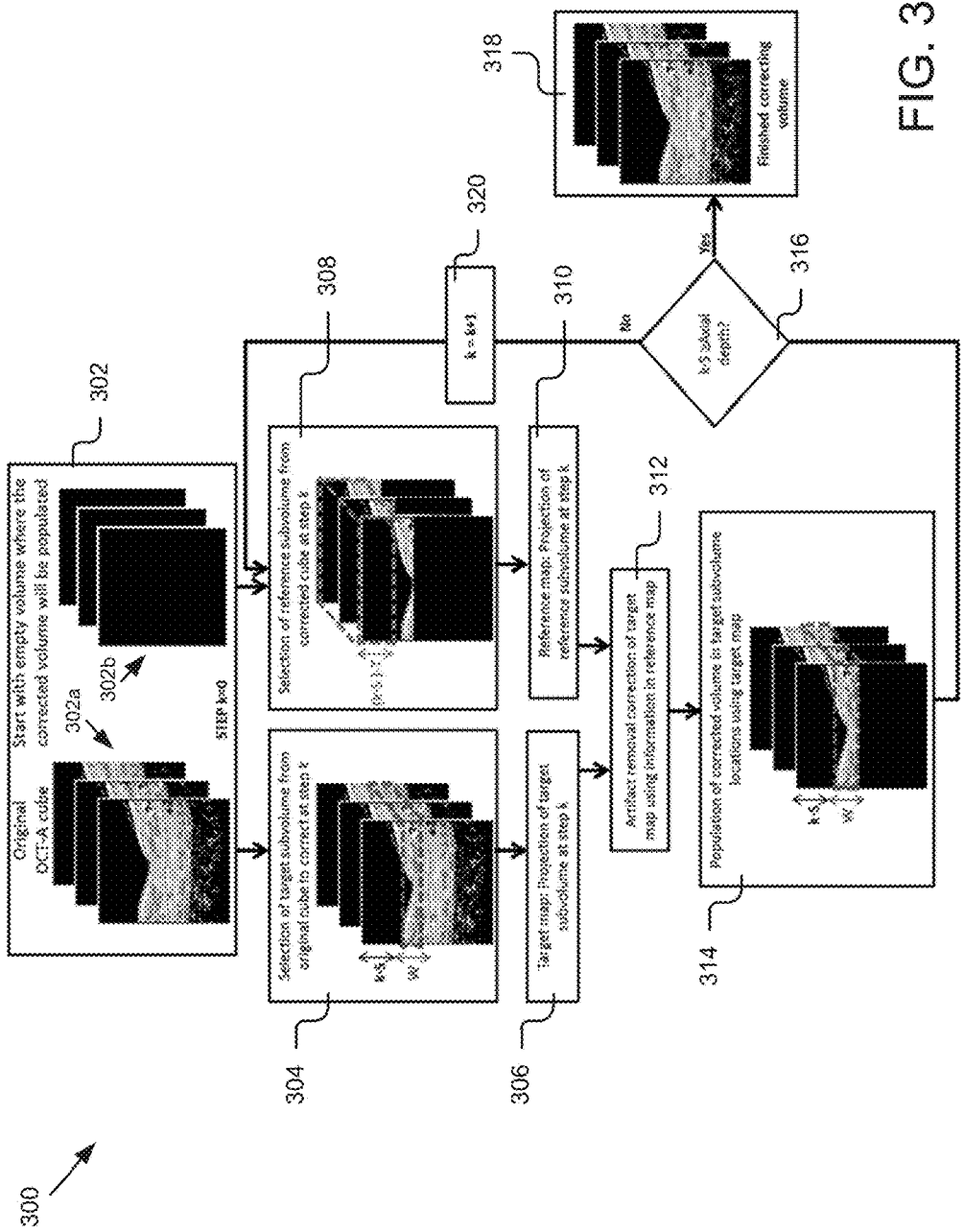
FIG. 3 is a flowchart of an example method 300 for the correction of decorrelation tail artifacts in a whole OCT-A volume according to one aspect of the present invention.

FIG. 3 is a flowchart of an example method 300 for the correction of decorrelation tail artifacts in a whole OCT-A volume according to one aspect of the present invention. It should be understood that the method 300 is not limited to the steps and/or operations embodied by this method and that other steps and/or operations are also possible and are within the scope of the present disclosure. The method 300 discussed here is an iterative process, with k indicating the iteration number. For instance, the first iteration may start here with k=0, the second iteration with k=k+1, and so on. That is, k tracks (e.g., counts) each iteration. The method 300 starts with obtaining an OCT-A volume (e.g., original uncorrected OCT-A cube) 302a and initializing an empty volume of the same dimensions to serve as corrected volume 302b, which will be populated/updated with corrected values on each iteration. 302a and 302b comprise the block 302. Next, in block 304, a target subvolume is defined from the uncorrected volume at axial positions started with a k·S depth (where S is a parameter indicating step size, which defines the number of pixels the location of the target slab is increased in depth at each iteration) and spanning in depth with a W axial width. Both the step size S and the axial width W can have a constant value throughout the iterations and/or span of the horizontal-vertical plane or can have values that are automatically adapted to the OCT data at each iteration or position in the horizontal-vertical plane. That is, both S and W may be variable. The target subvolume constitutes the locations in the original uncorrected volume that are partially corrected at each iteration. These locations are defined by a horizontal window of defined thickness W (which can be constant or automatically adapted to the data and/or iteration) that slides down (i.e., moves in an increasing depth direction (e.g., z-direction)) at each iteration with a step size of S (which can be constant or automatically adapted to the data and/or iteration). That is, at a particular iteration k, the target subvolume covers the axial positions situated between a k·S depth and a (k·S)+W depth. The thickness W is taken to be of small value at its maximum (e.g., ~20 microns) and the step size S may be greater than 0 and smaller or equal to W. A particular iteration k and its subsequent iteration k+1 may have a region of overlap of W-S. S may be set to 1 pixel for a pixel-by-pixel sliding window, but this value may be increased up to W to increase speed of the algorithm (although results may not be optimal).

In block 306, the target subvolume is projected onto a target map. The target map is formed by the axial summation of the original uncorrected cube data restricted to the region indicated by the target subvolume. The axial summation projection method is preferred as it produces adequate results. However, it should be understood that this is not limiting and other projection methods (e.g., a maximum projection) are also possible and within the scope of the present disclosure. Due to the nature of target maps and use in the correction workflow, it is important that the defined window thickness W is within some reasonable small ranges. A good consideration of a value for W would be for it to be large enough so that enough information is included to apply decorrelation tail removal in the target map and small enough to produce a result of enough (e.g. a predefined) resolution. Larger values of W could produce more severe axial smoothing effects in the corrected volume. A good rule of thumb for a configuration with S=1 is not to use a W value larger than the minimum diameter of the vessels that one aims to identify in the resulting corrected volume.

In block 308, a reference subvolume, which may have a variable depth span, is defined in volume 302b at axial positions, which may start from an upper position in (e.g., the top of) the volume and span to a depth defined by (k·S)−T, where T indicates a correction margin, which may be variable. The correction margin T can have a constant value throughout the iterations and/or span of the horizontal-vertical plane or can have values that are automatically adapted to the OCT data at each iteration or position in the horizontal-vertical plane. By the definition of this reference subvolume in each iteration, we make sure that we only use information that has already been fully corrected in the previous iteration. The reference subvolume constitutes upper (inner axial depths) locations in the corrected volume we want to consider as previously corrected information subject to produce decorrelation tail artifacts in the target subvolume region. One peculiarity of the reference subvolume is that it has to correspond to a region that has already been fully processed and corrected. This region is defined by a horizontal window from the top of the volume and spanning until a depth defined by (k·S)−T, where T indicates a correction margin. The correction margin T is defined to allow a small margin of separation between target volume and reference volume. This small margin of separation guarantees that we are not eliminating blood vessels that are partially present in the target subvolume and reference subvolume, an effect that could happen when the upper part of the vessel is used to correct the lower part and therefore partly suppresses the flow signal in the lower part. The correction margin T can take values larger or equal to 1 pixel with smaller values producing higher correction effects and larger values producing less corrections. Given the typical nature of blood vessels in the retina expanding in the horizontal-vertical plane, a good consideration of this value would be for it to be small enough to resolve separation between different levels of blood vessels and large enough so that a significant axial portion of an individual vessel is not included in both target and reference subvolumes. A good rule of thumb for a configuration with S=1 is not to use a T value smaller than the minimum separation of vessels at different levels but larger than half the minimum diameter of the vessels that are to be identified in the resulting volume.

Next, similar to target map formation in block 306, a reference map is formed by the axial summation of the updated corrected cube data restricted to the region indicated by the reference subvolume (block 310). As mentioned earlier, the axial summation projection method is preferred as it produces adequate results. However, it should be understood that this is not limiting and other projection methods (e.g., a maximum projection) are also possible and within the scope of the present disclosure.

Figure 4:
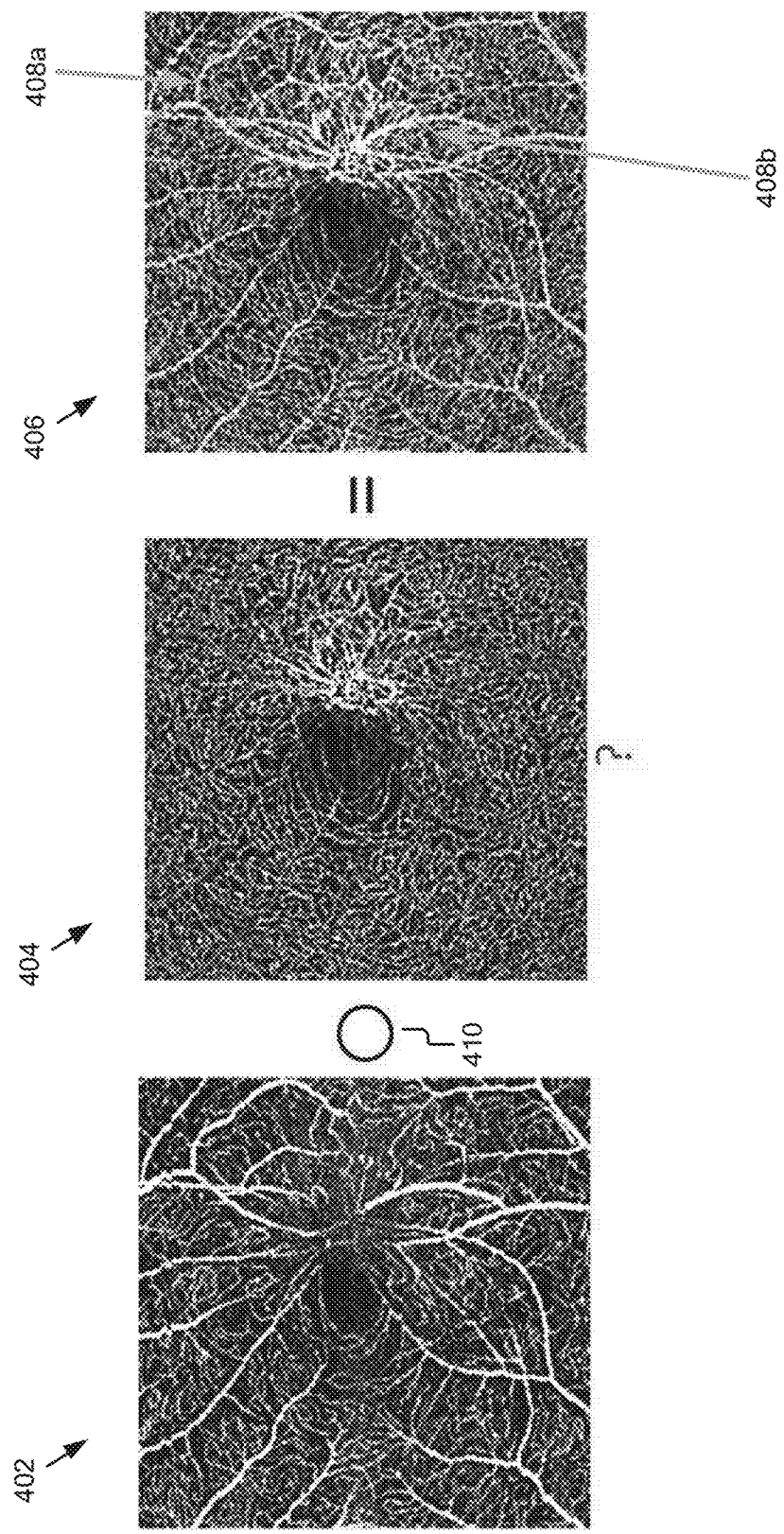
FIG. 4 illustrates an example of producing an artifact reduced image based on solving an inverse problem.

Once the target and reference maps are generated as discussed above in blocks 306 and 310, respectively, the method 300 then corrects decorrelation tail artifacts in the target map using information in the reference map (block 312). In one embodiment, the corrected target map (e.g., obtained from a deeper subvolume) is generated by mixing the information on the reference map (subvolume above the target map) and a target map without decorrelation tail artifacts (the unknown image to reconstruct) as shown for example in FIG. 4. The goal is to reconstruct an unknown image (version of the target map with reduced artifacts) given the original target map and the reference map (generated from information that has been already corrected in a previous step). This process can be formulated and solved as an inverse problem considering a particular mixing model. FIG. 4 depicts such an inverse problem scenario where an estimated unknown image 404 (i.e., target map with reduced artifacts) is generated given a reference map image 402 and the original target map image 406 having artifacts (e.g., artifacts 408a and 408b). Reference numeral 410 indicates the mixing between the reference map image 402 and the unknown image 404. Two common mixing models can be considered as follows:

Additive: each pixel of the uncorrected target map is assumed to be generated as a result of weighted reference map pixel with corrected target map pixel. The number of unknowns (weights for pixels of reference and target maps and the pixel values of the unknown image) is equal to m×n+1 where m and n are the number of rows and columns of a map.

Multiplicative: each pixel of uncorrected target map is assumed to be generated as a result of weighted multiplication of reference map with corrected target map (pixelwise). The number of unknowns for this model is m×n which can be still considered as a large scale problem. Multiplicative assumption makes the problem easier to solve since the equation system is linear.

It should be noted that the method 300 is not limited to the above mixing models and additional mixing models and other solutions are possible and are within the scope of the present disclosure. In a preferred embodiment, the additive mixing model is used given its advantages in speed, lack of further parameters to optimize, and satisfactory results. The target map correction method discussed herein could also be localized to subregions within the map that can be later stitched together in a weighted fashion to generate the corrected target map. This consideration of regional correction instead of a global correction of the whole map can also benefit the correction of widefield OCT-A cubes.

Once the target map or slab has been adequately corrected, the method 300 updates the corrected volume 302b by adding the weighted values of the corrected target map to locations indicated by the target subvolume in a pixel by pixel manner (block 314). Since we are adding values described in a two-dimensional to a three-dimensional subvolume, the W axial positions described in the same horizontal and vertical locations within the target subvolume are updated with the same pixel value of the corrected target map, but possibly weighted in a different manner. These weights are defined as a particular axial function described in the limits established by W, with weights adding up to the parameter S. Different options can be considered as a weighting function (for example, a Gaussian function centered at the center of the window W). Alternatively, all axial locations may have a weight of S/W, which produced adequate results.

By this consideration, each pixel in the final corrected OCT-A volume is populated by adding the results of W/S corrected target maps defined at different depths. This way, although a blurring effect can be produced by the span of W, the corrected vessels result with an expected round appearance.

Next, a determination is made (see step 316) as to whether the corrected volume is fully updated or populated with the weighted values at all the locations of the OCT-A cube (i.e., $k \cdot S \geq$ axial depth of the cube). If the result of the determination is affirmative, then the method 300 ends by providing the finished corrected volume for display or a further analysis thereof (block 318). Otherwise, the method 300 continues with the next iteration (k=k+1, see block 320) to process or correct the next location of the OCT-A volume thereon. In some embodiments, the operations discussed herein with respect to blocks 302-320 of the method 300 may be performed by the artifacts correction module 1006 of the computer system 1000 (see FIG. 11).

In some embodiments, the finished corrected volume can be used for the visualization of one or more pathologies in an eye. For instance, an optimal slab may be produced by segmenting the corrected volume to identify different retinal layer boundaries. The optimal slab may be predefined by an upper limit or layer boundary and a lower limit or layer boundary. By way of an example, an optimal slab may be defined by taking outer plexiform layer (OPL) as the upper limit and retinal pigment epithelium (RPE) or Bruch's membrane as the lower limit. An enface projection of such an optimal slab defined within these two limits or boundaries can be used to visualize choroidal neovascularization (CNV). Producing an optimal slab from the corrected volume is advantageous as the decorrelation tail artifact(s) in the volume have already been corrected using the method 300 discussed herein and the chances of segmentation error(s) in such a corrected volume are minimal.

Correction Limits within the Volume:

In an alternative embodiment, a consideration of start and end points in the regions of interest where blood vessels are expected can speed the process by reducing the number of steps needed. Due to the nature of the retina in OCT-A volumes, presenting no significant information in the vitreous and past the choroid region, a reliable method to establish these limits is to consider a retinal centroid surface and displace it upwards and downwards to consider as top and bottom limits, respectively. The amount of displacement in each direction should be so that the top of the ILM and the bottom of the choroid is included within these limits plus a small margin. This small margin is considered to reduce initialization and bottom effects and should be of at least W+S.

Example Illustrations

Figure 5B:
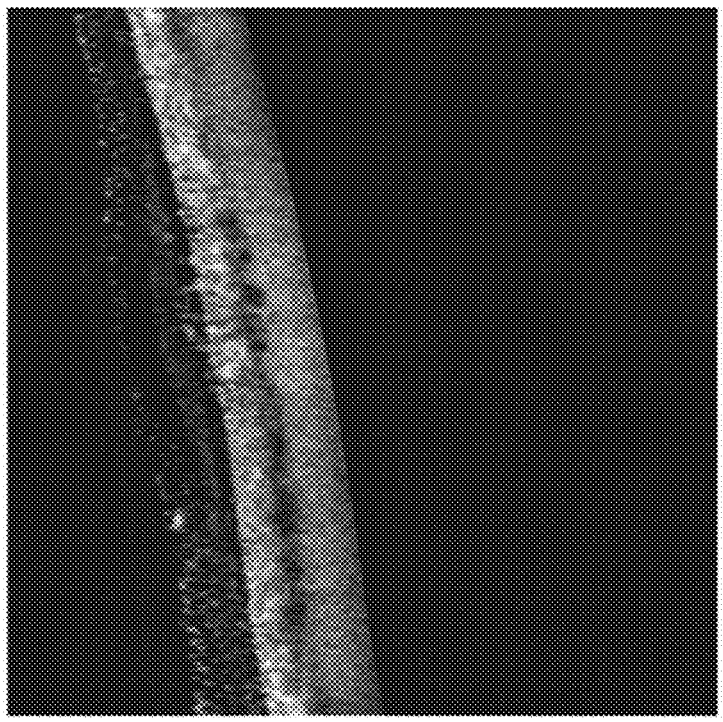
FIG. 5B shows a corrected version of the same fast B-scan after applying the decorrelation tail artifact correction method of the present application.
Figure 5A:
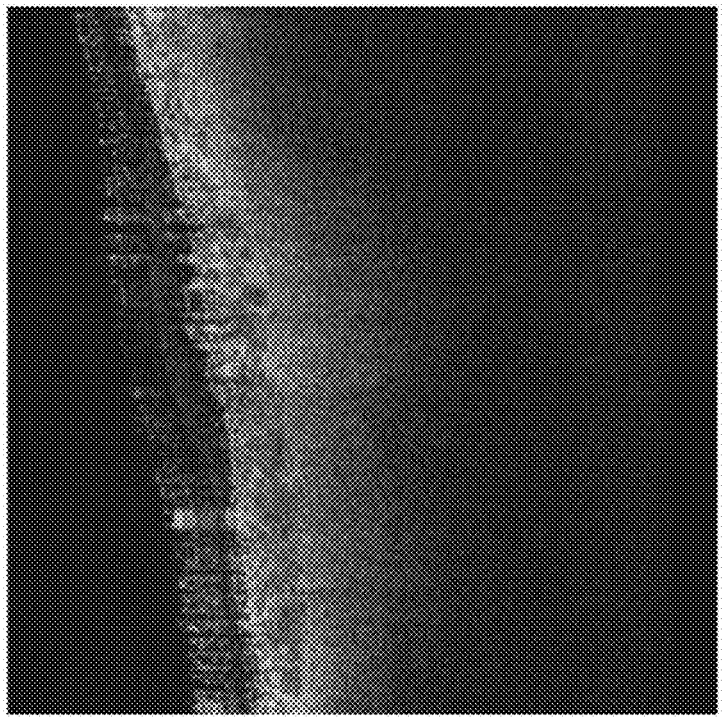
FIG. 5A shows an original uncorrected fast B-scan at the center of an OCT-A cube before decorrelation tail artifacts correction.
Figure 6B:
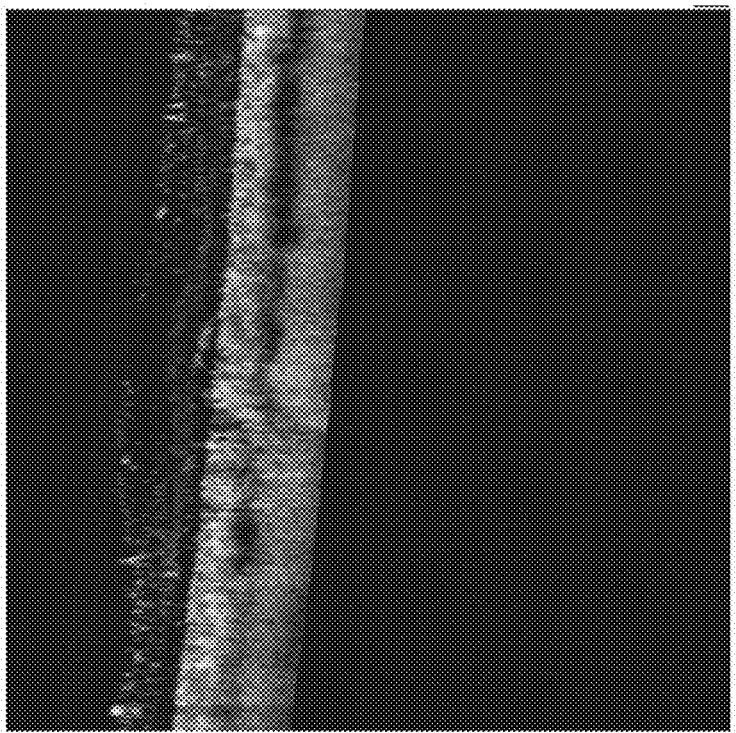
FIG. 6B shows a corrected version of the same slow B-scan after applying the decorrelation tail artifact correction method of the present application.
Figure 6A:
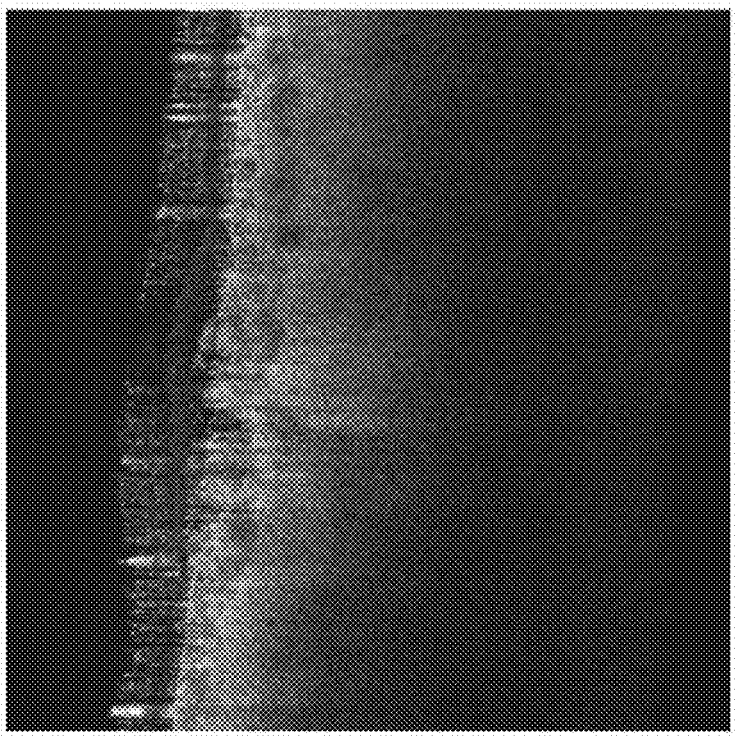
FIG. 6A shows an original uncorrected slow B-scan at the center of the OCT-A cube before decorrelation tail artifacts correction.

A set of preliminary results for an example OCT-A cube is shown with respect to FIGS. 5A-B and 6A-B. In particular, FIGS. 5A and 5B show a fast B-scan at the center of the cube before and after the decorrelation tail artifact correction, respectively. FIGS. 6A and 6B show the corresponding center slow B-scan before and after the decorrelation tail correction, respectively. Note that the cube has only been corrected within specified limits.

FIGS. 7 to 9 provide OCT-A examples comparing the artifact-correcting efficacy of the traditional slab-based correction method versus the OCT-A volume correction method of the present disclosure. In each case, the corrected slab produced by the present OCT-A volume correction method is shown to have fewer artifacts (e.g., decorrelation tail artifacts) than that produced by the traditional slab-based correction method.

Figures 7A, 7B, 7C:
FIGS. 7A-C show three different results of a deep retina slab generated from the same OCT-A cube. In particular.

FIGS. 7A-C show three different results of a deep retina slab generated from the same OCT-A cube. In particular, FIG. 7A shows the originally produced slab with (decorrelation tail) artifacts. FIG. 7B shows the slab after applying the traditional slab-based correction method, and FIG. 7C shows the slab after applying the OCT-A volume correction method of the present disclosure. As shown, the corrected slab of FIG. 7C demonstrates fewer (and less pronounced) decorrelation tail (e.g., projection) artifacts than that of FIG. 7B.

Figures 8A, 8B, 8C:
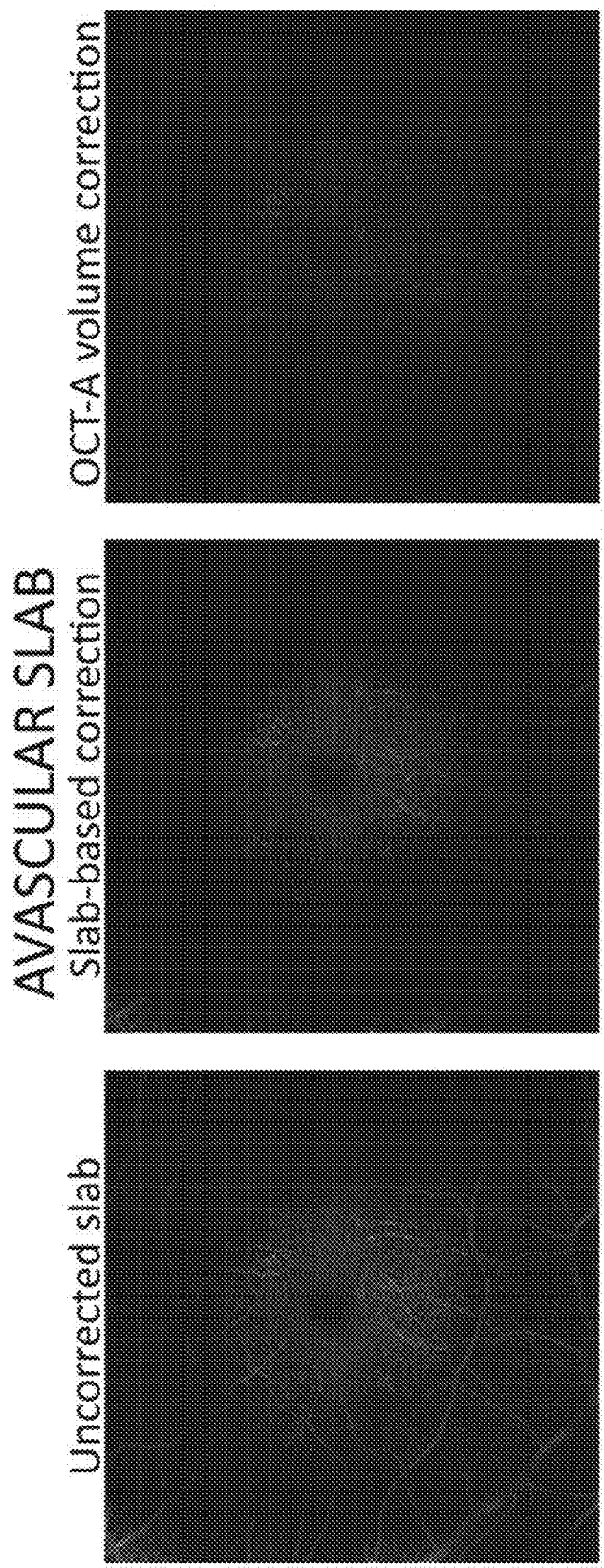
FIGS. 8A-C show three different results of an avascular slab generated from the same OCT-A cube. In particular.

FIG. 8A-C show three different results of an avascular slab generated from the same OCT-A cube. In particular, FIG. 8A shows the originally produced slab with artifacts. FIG. 8B shows the slab after applying the traditional slab-based correction method, and FIG. 8C shows the slab after applying the OCT-A volume correction method of the present disclosure. Again, the corrected slab of FIG. 8C shows a drastic reduction in artifacts (e.g., projected blood vessels) over that of FIG. 8B.

Figures 9A, 9B, 9C:
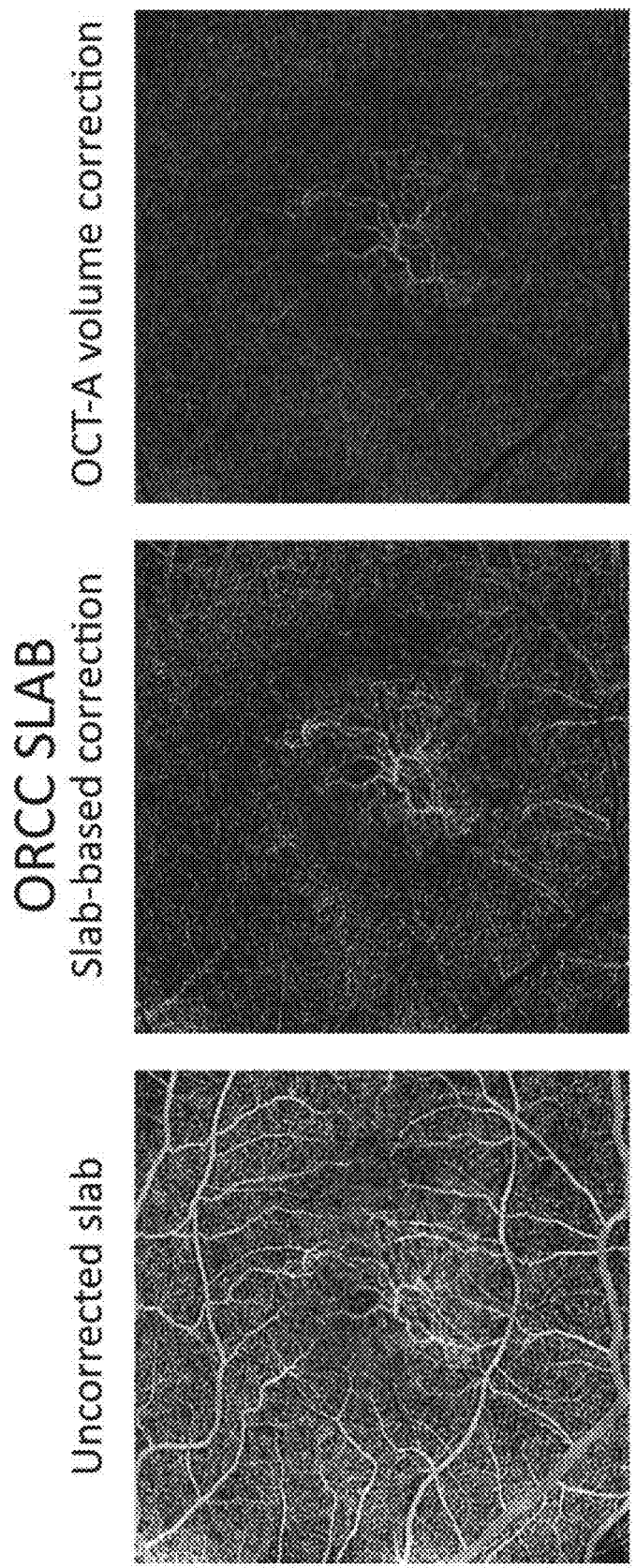
FIGS. 9A-C show three different results of an outer retina to choriocapillaris (ORCC) slab generated from the same OCT-A cube. In particular.

FIGS. 9A-C show three different results of a choriocapillaris (ORCC) slab generated from the same OCT-A cube. In particular, FIG. 9A shows the originally produced slab with artifacts. FIG. 9B shows the slab after applying the traditional slab-based correction method, and FIG. 9C shows the slab after applying the OCT-A volume correction method of the present disclosure. As is evident from the figures, the present OCT-A volume correction method achieves a greater degree of artifact correction (see FIG. 9C) than that provided by the traditional slab-based correction method (see FIG. 9B).

Figure 10:
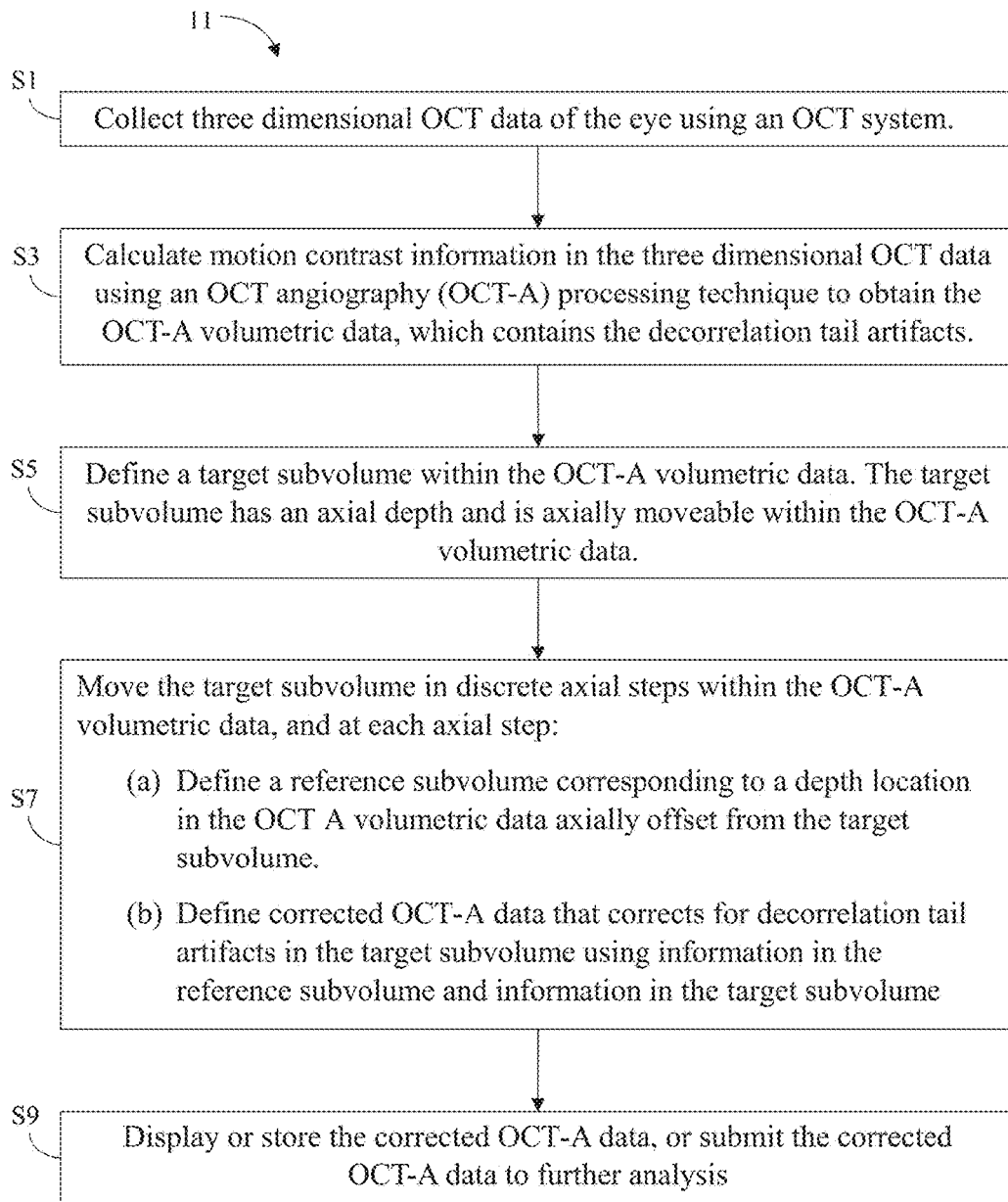
FIG. 10 illustrates an example method for correcting decorrelation tail artifacts in optical coherence tomography (OCT) angiography volumetric data of an eye.

FIG. 10 illustrates an example method 11 for correcting decorrelation tail artifacts in optical coherence tomography (OCT) angiography volumetric data of an eye. The method may begin at step S1, where three dimensional OCT data of the eye is collected, for example by using an OCT system; the collecting step may include accessing a data store of previously collected OCT volumetric data. At step S3, motion contrast information in the three dimensional OCT data is calculated using an OCT angiography (OCT-A) processing technique to obtain the OCT-A volumetric data, which may contain the decorrelation tail artifacts. In step S5, a target subvolume is defined within the OCT-A volumetric data. The target subvolume has an axial depth and is axially moveable within (e.g., at least within a partial depth range of) the OCT-A volumetric data. At step S7, the target subvolume is moved in discrete axial steps (e.g., in the z-direction) within the OCT-A volumetric data, and the following two sub-steps may be executed at each axial step. In a first sub-step (a), a reference subvolume corresponding to a depth location (e.g., an axial location) within the OCT-A volumetric data is defined axially offset from the target subvolume. The reference subvolume may be defined within the OCT-A volumetric data itself, or may be defined within another volumetric data, such as one defined by a collection of previously corrected OCT-A data (see e.g., FIG. 3). The depth location of the reference subvolume may be such that the reference subvolume is above or below the target subvolume, and may at least partially overlap or completely avoid the target subvolume. In a second sub-step (b), corrected OCT-A data that corrects for decorrelation tail artifacts in the target subvolume is defined using a combination of information in the reference subvolume and information in the target subvolume. The information in the reference subvolume may include previously corrected OCT-A data, or non-corrected OCT-A data, or a combination of the two. For example, the reference subvolume may define a region within uncorrected OCT-A volumetric data, or define a region within the OCT-A volumetric data that has been corrected, or define a region within another OCT-A data that includes a collection of previously corrected OCT-A data.

Some embodiments may repeat one or more steps of the methods of FIG. 10, where appropriate. Although this disclosure describes and illustrates particular steps of the method of FIG. 10 as occurring in a particular order, this disclosure contemplates any suitable steps occurring in any suitable order.

Example Computer System

Figure 11:
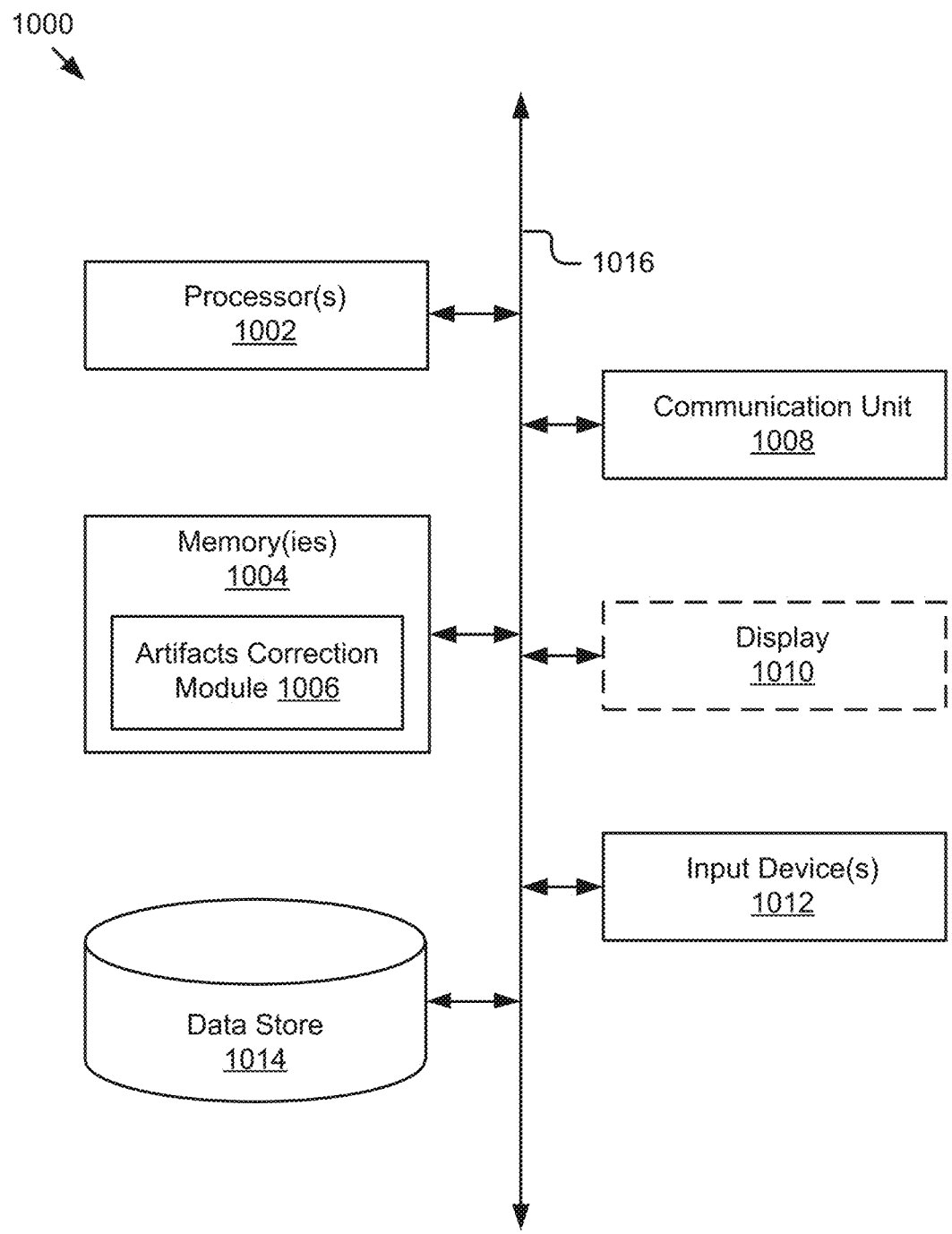
FIG. 11 is a block diagram of a general computer system that may perform the functions discussed in this disclosure according to one aspect of the present invention.

The processing unit 221 that has been discussed herein in reference to FIG. 2 can be implemented with a computer system configured to perform the functions that have been described herein for this unit. For instance, the processing unit 221 can be implemented with the computer system 1000, as shown in FIG. 11. The computer system 1000 may include one or more processors 1002, one or more memories 1004, a communication unit 1008, an optional display 1010, one or more input devices 1012, and a data store 1014. The display 1010 is shown with dotted lines to indicate it is an optional component, which, in some instances, may not be a part of the computer system 1000. In some embodiments, the display 1010 discussed herein is the display 222 that has been discussed herein in reference to FIG. 2.

The components 1002, 1004, 1008, 1010, 1012, and 1014 are communicatively coupled via a communication or system bus 1016. The bus 1016 can include a conventional communication bus for transferring data between components of a computing device or between computing devices. It should be understood that the computing system 1000 described herein is not limited to these components and may include various operating systems, sensors, video processing components, input/output ports, user interface devices (e.g., keyboards, pointing devices, displays, microphones, sound reproduction systems, and/or touch screens), additional processors, and other physical configurations.

The processor(s) 1002 may execute various hardware and/or software logic, such as software instructions, by performing various input/output, logical, and/or mathematical operations. The processor(s) 1002 may have various computing architectures to process data signals including, for example, a complex instruction set computer (CISC) architecture, a reduced instruction set computer (RISC) architecture, and/or architecture implementing a combination of instruction sets. The processor(s) 1002 may be physical and/or virtual, and may include a single core or plurality of processing units and/or cores. In some embodiments, the processor(s) 1002 may be capable of generating and providing electronic display signals to a display device, such as the display 1010, supporting the display of images, capturing and transmitting images, performing complex tasks including various types of feature extraction and sampling, etc. In some embodiments, the processor(s) 1002 may be coupled to the memory(ies) 1004 via a data/communication bus to access data and instructions therefrom and store data therein. The bus 1016 may couple the processor(s) 1002 to the other components of the computer system 1000, for example, the memory(ies) 1004, the communication unit 1008, or the data store 1014.

The memory(ies) 1004 may store instructions and/or data that may be executed by the processor(s) 1002. In the depicted embodiment, the memory(ies) 1004 stores at least an artifacts correction module 1006, which may include software, code, logic, or routines for performing any and/or all of the techniques described herein. For instance, the artifacts correction module 1006 may perform all or some of the operations depicted in FIG. 3. In some embodiments, the memory(ies) 1004 may also be capable of storing other instructions and data including, for example, an operating system, hardware drivers, other software applications, databases, etc. The memory(ies) 1004 are coupled to the bus 1016 for communication with the processor(s) 1002 and other components of the computer system 1000. The memory(ies) 1004 may include a non-transitory computer-usable (e.g., readable, writeable, etc.) medium, which can be any apparatus or device that can contain, store, communicate, propagate or transport instructions, data, computer programs, software, code, routines, etc. for processing by or in connection with the processor(s) 1002. A non-transitory computer-usable storage medium may include any and/or all computer-usable storage media. In some embodiments, the memory(ies) 1004 may include volatile memory, non-volatile memory, or both. For example, the memory(ies) 1004 may include a dynamic random access memory (DRAM) device, a static random access memory (SRAM) device, flash memory, a hard disk drive, a floppy disk drive, a CD ROM device, a DVD ROM device, a DVD RAM device, a DVD RW device, a flash memory device, or any other mass storage device known for storing instructions on a more permanent basis.

The computer system for the processing unit 221 may include one or more computers or processing units at the same or different locations. When at different locations, the computers may be configured to communicate with one another through a wired and/or wireless network communication system, such as the communication unit 1008. The communication unit 1008 may include network interface devices (I/F) for wired and wireless connectivity. For example, the communication unit 1008 may include a CAT-type interface, USB interface, or SD interface, transceivers for sending and receiving signals using Wi-Fi™; Bluetooth®, or cellular communications for wireless communication, etc. The communication unit 1008 can link the processor(s) 1002 to a computer network that may in turn be coupled to other processing systems.

The display 1010 represents any device equipped to display electronic images and data as described herein. The display 1010 may be any of a conventional display device, monitor or screen, such as an organic light-emitting diode (OLED) display, a liquid crystal display (LCD). In some embodiments, the display 1010 is a touch-screen display capable of receiving input from one or more fingers of a user. For example, the device 1010 may be a capacitive touch-screen display capable of detecting and interpreting multiple points of contact with the display surface.

The input device(s) 1012 are any devices for inputting data on the computer system 1000. In some embodiments, an input device is a touch-screen display capable of receiving input from one or more fingers of the user. The functionality of the input device(s) 1012 and the display 1010 may be integrated, and a user of the computer system 1000 may interact with the system by contacting a surface of the display 1010 using one or more fingers. In other embodiments, an input device is a separate peripheral device or combination of devices. For example, the input device(s) 1012 may include a keyboard (e.g., a QWERTY keyboard) and a pointing device (e.g., a mouse or touchpad). The input device(s) 1012 may also include a microphone, a web camera, or other similar audio or video capture devices.

The data store 1014 can be an information source capable of storing and providing access to data. In the depicted embodiment, the data store 1014 is coupled for communication with the components 1002, 1004, 1008, 1010, and 1012 of the computer system 1000 via the bus 1016, and coupled, via the processor(s) 1002, for communication with the artifacts correction module 1006. In some embodiments, the artifacts correction module 1006 is configured to manipulate, i.e., store, query, update, and/or delete, data stored in the data store 1014 using programmatic operations.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

Furthermore, the description can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof.

We claim:

1. A method for correcting decorrelation tail artifacts in optical coherence tomography (OCT) angiography volumetric data of an eye, said method comprising:
    collecting three dimensional OCT data of the eye using an OCT system;
    calculating motion contrast information in the three dimensional OCT data using an OCT angiography (OCT-A) processing technique to obtain the OCT-A volumetric data containing the decorrelation tail artifacts;
    defining a target subvolume within the OCT-A volumetric data, the target subvolume having an axial depth and being axially moveable within the OCT-A volumetric data;
    moving the target subvolume in discrete axial steps within the OCT-A volumetric data, and at each axial step:
        (a) defining a reference subvolume corresponding to a depth location in the OCT-A volumetric data axially offset from the target subvolume;
        (b) defining corrected OCT-A data that corrects for decorrelation tail artifacts in the target subvolume using information in the reference subvolume and information in the target subvolume; and
    displaying or storing the corrected OCT-A data or a further analysis thereof.

2. The method as recited in claim 1, wherein the reference subvolume contains corrected OCT-A data from a previous axial step.

3. The method as recited in claim 1, wherein the step of defining corrected OCT-A data comprises:
    using an inverse calculation, determining a corrected subvolume that can be mixed with the reference subvolume to generate the target subvolume, said corrected subvolume being said corrected OCT-A data.

4. The method as recited in claim 3, wherein the inverse calculation uses one or more of an additive mixing, a multiplicative mixing, and a combination of the two for determining the corrected subvolume that can be mixed with the reference subvolume to generate the target subvolume.

5. The method as recited in claim 1, further comprising at each axial step:
    (c) determining a positional correspondence between the defined corrected OCT-A data and the OCT-A volumetric data within the target subvolume;
    (d) updating OCT-A volumetric data within the target subvolume based on its corresponding corrected OCT-A data;
    wherein the reference subvolume is defined within the OCT-A volumetric data.

6. The method as recited in claim 1, further comprising:
    initializing an empty volume to serve as a corrected OCT-A volume; and
    at each axial step:
    (c) updating the corrected OCT-A volume with the defined corrected OCT-A data at an updated depth location within the corrected OCT-A volume, and mapping the updated depth location with the corrected OCT-A volume to the current depth location of the target subvolume within the OCT-A volumetric data.

7. The method as recited in claim 6, wherein the reference subvolume is defined within the corrected OCT-A volume.

8. The method as recited in claim 1, wherein step (b) of defining corrected OCT-A data includes:
    projecting the target subvolume to a corresponding target map and projecting the reference subvolume to a corresponding reference map using a projection technique; and
    correcting decorrelation tail artifacts in the target map, to define a corrected target map, using information in the reference map and in the target map;
    wherein the defining of the corrected OCT-A data is based on the corrected target map.

9. The method as recited in claim 8, wherein defining of the corrected OCT-A data further includes adding weighted values of the corrected target map to locations in the corrected OCT-A data indicated by the target subvolume in a pixel by pixel manner.

10. The method as recited in claim 8, wherein the projection technique is axial summation of data corresponding to a region indicated by the target subvolume for the target map and axial summation of data corresponding to a region indicated by the reference subvolume for the reference map.

11. The method as recited in claim 1, further comprising:
segmenting the corrected OCT-A data to define a segmented output identifying two or more retinal layer boundaries located at different depth locations in the eye;
generating an optimal slab from the segmented output, said optimal slab defined by an upper layer boundary and a lower layer boundary, wherein the optimal slab visualizes a particular pathology in the eye; and
displaying or storing the optimal slab or a further analysis thereof.

12. The method as recited in claim 11, wherein the pathology is choroidal neovascularization (CNV).

13. The method as recited in claim 11, wherein the upper layer boundary is outer plexiform layer (OPL) and the lower layer boundary is retinal pigment epithelium (RPE).

14. The method as recited in claim 11, wherein the segmented output is free from segmentation errors.

15. The method as recited in claim 1, wherein the three dimensional OCT data contains multiple B-scans taken at approximately the same set of transverse locations on a particular region of the eye, and the target subvolume includes one or more A-scans.

16. The method as recited in claim 1, wherein the OCT-A processing technique is one or more of an intensity-based processing technique, a phase-based processing technique, and a complex-based processing technique.

17. The method as recited in claim 1, wherein the axial depth of the target subvolume is variable at each axial step.

18. The method as recited in claim 1, wherein an axial distance that the target subvolume moves between discrete axial steps is variable.

19. The method of as recited in claim 1, wherein a current axial position of the target subvolume is define as $k*S$, where k tracks axial movements of the target subvolume and S is a depth displacement multiplier for each axial movement of the target subvolume.

20. The method as recited in claim 19, wherein a current axial position of the reference subvolume corresponds to a depth position in the OCT-A volumetric data defined as $(k*S-T)$, where T is a correction margin that defines the axial offset from the target subvolume, and T is variable at each axial step.

* * * * *

UNITED STATES PATENT AND TRADEMARK OFFICE
CERTIFICATE OF CORRECTION

PATENT NO. : 10,441,164 B1
APPLICATION NO. : 15/914933
DATED : October 15, 2019
INVENTOR(S) : Luis De Sisternes et al.

Page 1 of 1

It is certified that error appears in the above-identified patent and that said Letters Patent is hereby corrected as shown below:

In the Specification

In Column 14, Line 31, delete "FIG." and insert -- FIGS. --, therefor.

In the Claims

In Column 20, Line 15, in Claim 19, after "method" delete "of".

Signed and Sealed this
Twenty-fifth Day of February, 2020

Andrei Iancu
*Director of the United States Patent and Trademark Office*